(12) United States Patent
Le Moel et al.

(10) Patent No.: US 6,517,858 B1
(45) Date of Patent: Feb. 11, 2003

(54) BIOACTIVE PROSTHESES WITH IMMUNOSUPPRESSIVE, ANTISTENOTIC AND ANTITHROMBOTIC PROPERTIES

(75) Inventors: Alain Le Moel, Chaville (FR); Natacha Betz, Boulogne-Billancourt (FR); Christophe Bureau, Les Ulis (FR); Guy Deniau, Auffargis (FR); Charles Baquey, Le Haillan (FR); Gérard Deleris, Bordeaux (FR); Werner Haberbosch, Giessen (DE)

(73) Assignees: Commissariat a L'Energie Atomique, Paris (FR); Institut National de la Sante et de la Recherche Medicale, Paris (FR); Kerckhoff-Klinik GmbH, Bad Nauheim (DE)

( * ) Notice: Subject to any disclaimer, the term of this patent is extended or adjusted under 35 U.S.C. 154(b) by 0 days.

(21) Appl. No.: 09/831,948

(22) PCT Filed: Nov. 15, 1999

(86) PCT No.: PCT/FR99/02795
§ 371 (c)(1),
(2), (4) Date: May 16, 2001

(87) PCT Pub. No.: WO00/29043
PCT Pub. Date: May 25, 2000

(30) Foreign Application Priority Data

Nov. 16, 1998 (FR) .............................. 98 14351

(51) Int. Cl.⁷ ............................. A61F 2/00; A61F 13/00; A61K 9/14
(52) U.S. Cl. ...................... 424/424; 424/422; 424/486; 424/488; 424/484
(58) Field of Search ................................. 424/424, 422, 424/486, 488, 484; 623/1.15, 1.42

(56) References Cited

U.S. PATENT DOCUMENTS

| 4,879,135 A | | 11/1989 | Greco et al. | |
|---|---|---|---|---|
| 6,248,127 B1 | * | 6/2001 | Shah et al. | ................. 623/1.15 |
| 6,254,634 B1 | * | 7/2001 | Anderson et al. | .......... 623/1.42 |

FOREIGN PATENT DOCUMENTS

| EP | 0 596 615 | * | 5/1994 |
|---|---|---|---|
| EP | 0 832 618 | | 4/1998 |
| EP | 0 873 732 | * | 10/1998 |
| EP | 0 940 144 | | 9/1999 |
| FR | 2 187 849 | | 1/1974 |

OTHER PUBLICATIONS

Dupuy et al. "Association of Polyacrylamide Beads to polyethylene Terephthalate Prostheses" Biomat., Art. Cells & Immob. Biotech., 21, No. 4, 1993, pp. 553–561.*
C. Degert, et al., Biomat., Art. Cells & Immob. Biotech., vol.21, No. 4, pp. 553–561, "Association of Polyacrylamide Beads to Polyethylene Terephtalate Prostheses", 1993.
Ch. Baquey, et al., Inov. Tech. Biol. Med., vol. 2, No. 4, pp. 378–389, "Interet Du Greffage Radiochimique De Monomeres Vinyliques Pour Ameliorer L'Hemocompatibilite Des Materiaux Artificiels", 1981.
P. Viel, et al., Journal of Electroanalytical Chemistry, vol. 470, pp. 14–22, "Electropolymerization of Methacrylonitrile on a Rotating Disk Electrode at High Spinning Rate", 1999.
J. Charlier, et al., Journal of Electroanalytical Chemisty, vol. 465, pp. 200–208, "Electropolymerization of methacrylonitrile and N–vinyl–2–Pyrrolidone as Probed by an EQCM", 1999.
C. Bureau, et al., J. Adhesion, vol. 58, pp. 101–121, "Electrochemistry as a tool to Monitor Lewis Acid–Base Reactions Between Methacrylonitrile and Metallic Surfaces: A Theoretical and Experimental Proposal", 1996.
C. Bureau, et al., Macromolecules, vol. 30, No. 2, pp. 333–336, "Comments on "The Electroreduction of Acrylonitrile: A New Insight into the Mechanism" by Mertens et al", 1997.

* cited by examiner

Primary Examiner—Thurman K. Page
Assistant Examiner—Blessing Fubara
(74) Attorney, Agent, or Firm—Oblon, Spivak, McClelland, Maier & Neustadt, P.C.

(57) ABSTRACT

The invention relates to a bioactive implant comprising a substrate coated with a polymer layer with reactive functions, and a bioactive substance fixed on the implant by means of said reactive functions to enable progressive release on the implant site.

Such implants are useful in the field of cardiology for example to prevent restenosis resulting from the fitting of stents in the coronary arteries.

24 Claims, No Drawings

BIOACTIVE PROSTHESES WITH IMMUNOSUPPRESSIVE, ANTISTENOTIC AND ANTITHROMBOTIC PROPERTIES

DISCLOSURE

1. Field of the Invention

The present invention relates to bioactive implants, particularly with immunosuppressive, antistenotic and antithrombotic properties.

Such implants may be used in the field of cardiology and vascular surgery as artery substitutes or as stents placed in arteries, particularly in coronary arteries, to prevent any risk of thrombosis or restenosis.

Bioactive implants may also be used in numerous other fields where it is important to give the implant an additional property due to the presence of a bioactive substance.

2. State of the Related Art

In the field of cardiology, stenosis is usually treated by angioplasty, i.e. by inserting, into the artery concerned, a balloon which is inflated at high pressure in contact with the stricture in order to eliminate it. Following the angioplasty, a stent, which prevents the recurrence of stenosis, may be placed in the artery concerned. However, a complication associated with the use of said stents results from the growth of new neo-tissue and intimal hyperplasia which may induce an obstruction of the artery and restenosis due the presence of the stent.

The fitting of coronary stents plays an increasingly important role in the treatment of chronic coronary disease, but to date said stents have been unable to solve the problem of restenosis and restenosis rates after fitting of stents are still 22 to 32%. As mentioned above, said restenosis is the result of neo-intimal tissue proliferation which needs to be prevented.

In addition, it would be very beneficial to have implants, particularly coronary stents, which would make it possible to prevent said tissue proliferation.

It has already been envisaged to treat implants to fill them with bioactive substances giving them antithrombotic and antimicrobial properties.

In this way, the document EP-A-596 615 [1] discloses implants with a polymer substrate which are coated with a layer of grafted polymer containing an active product.

Such implants are unsuitable for use as stents since the polymer substrates do not have the required mechanical characteristics.

For implants with metallic substrates, reliable and durable fixation of an active product on the implant is more difficult to apply.

The document EP-A-0 873 732 [2] discloses a stent on which heparin is fixed, by means of a coating comprising functional groups attracting the heparin obtained for example by means of a methane plasma and an ammonia gas plasma or amine type monomer.

The document US-A-4879 132 [3] discloses implants on which a medicinal product is fixed, by means of an anionic surfactant.

The document EP-A-0 832 618 [4] discloses stents with long-term antithrombotic properties, which comprises a metallic substrate on which heparin is fixed for example by means of a coupling agent or a cross-linking agent, after oxidation of the metal surface.

Thus, none of these techniques can be used to bind the coating containing the active substance with the metal substrate with a durable and reliable covalent bond.

The present invention specifically relates to new implants which do not induce this disadvantage.

In addition, none of the approaches disclosed to date mention the use of grafted bioactive substances with antirestenotic properties, while restenosis represents one of major undesirable local responses in the case of stent fitting. Thus, the aim of the present invention is also to give the coatings the possibility to prevent restenosis.

DESCRIPTION OF THE INVENTION

In this way, the invention relates to a bioactive implant comprising a substrate wherein the surface is made of a material chosen from metals, metallic alloys, semiconductor materials, conductive polymers, composite materials, ceramics, carbon fibres and their mixtures, said surface being coated with a polymer or copolymer layer with reactive functions grafted by means of a covalent bond on the substrate surface and a bioactive substance fixed on the implant by means of said reactive functions to enable progressive release on an implant site.

Said implant thus shows an additional property due to the presence of a suitable bioactive substance, which is used to treat or prevent, directly on the implant site, the development of undesirable phenomena.

According to the invention, the surface of the substrate of the implant is made of a material which may be a metal, a metallic alloy, a conductive polymer, a semi-conductor material, an organic composite material, a ceramic, an oxide, carbon fibres, or their mixtures.

The substrate may be made entirely of any of said materials or comprise a core made of any type of material surrounded by a layer of any of the materials defined above.

The metals and metallic alloys are selected, for example, from stainless steels, cobalt or titanium-based alloys, shape-retentive alloys, noble metals such as gold or platinum and noble metal alloys.

The conductive polymers that may be used in the invention to form the surface of the substrate may be of various types. Examples include conductive polymers formed from monomers such as pyrrole, thiophene, aniline or their functionalised or non-functionalised derivatives, and the copolymers of the monomers mentioned above.

The ceramic materials that may be used for the surface of the substrate may be for example aluminium oxide, glass, hydroxyapatite, carbides and nitrides and any surface oxide, either native or deposited on the surface by any means.

The composite materials that may be used may be materials such as metals and polymers coated with ceramic or carbon or associated with carbon fibres and organic polymer-based materials reinforced with inorganic fibres such as glass or carbon fibres.

The material used for the implant substrate is selected essentially as a function of required mechanical properties of the implant.

In the case of stents intended for cardiology, a metallic substrate, for example made of stainless steel or shape-retentive metallic alloy, is advantageously used.

According to the invention, the surface of the substrate of the implant is coated with a polymer or copolymer layer with reactive functions, the purpose of which is to retain temporarily a bioactive substance which will then be released on the implant site.

In the remainder of the present document, the term polymer refers not only to a polymer based on identical monomers but also a copolymer based on different monomers.

The suitable reactive functions for said fixation may be chosen, for example, from the acid, ester, amide, amine and hydroxyl functions.

The polymer used to form this layer must be biocompatible. It is possible to use, in particular, vinyl monomer polymers and/or copolymers, functionalised or not, dextran, conductive polymers and any polymer or copolymer formed from mixtures of vinyl monomers and/or conductive polymer precursor monomers, functionalised or not. Examples of such polymers include acrylic and methacrylic polymers such as polymethyl methacrylate, polyethyl methacrylate, polyacrylic acid, polymethacrylic acid, poly(hydroxyethyl methacrylate) and polyacrylamide, polyvinyl alcohol, poly (4-vinylpyridine), dextran, polystyrene, conductive polymers based on thiophene, aniline, pyrrole, and any polymer or copolymer using monomers obtained by functionalisation of the above-mentioned monomers. Such polymers comprise or may comprise suitable reactive functions, chosen as a function of the biological substance fixation method.

According to the invention, the bioactive substance may be fixed directly on the reactive functions of the polymer layer by a covalent bond with possible insertion of a spacer between the reactive functions and the substance.

The bioactive substance may also be fixed on the reactive functions of the polymer layer by means of microreservoirs containing said substance, which are fixed on the reactive functions of the layer.

Said microreservoirs may comprise a microporous outer membrane which is coupled with the reactive functions of the polymer layer.

For example, said microporous membrane may be made of polyacrylamide.

It is also possible to use, as microreservoirs, agar beads filled directly with the bioactive substance or filled with spherulites in turn filled with the bioactive substance.

The bioactive substance used is chosen as a function of the desired properties of the implant. Said bioactive substance may belong for example to the group of antimitotic, antiaggregation, antiinflammatory, antirestenotic, antithrombotic, immunosuppressive, antirejection and antibiotic compounds. It is also possible to use a reverse oligonucleotide as the bioactive substance.

Indeed, such oligonucleotides may act as a decoy for mRNA and form targets for cell proliferation genes at various levels. In the case of heart implants, they may oppose the proliferation of smooth muscle cells.

In the case of bioactive implants intended for cardiology, the bioactive substance may be chosen in particular from cyclosporin, rapamycin, aspirin, ticlopidine, 3-deazaadenosine and MCP-1.

MCP-1 is the chemotactic protein for macrophases.

Cyclosporin is an immunosuppressive agent which inhibits the expression of the tissue factor in stimulated monocytes and smooth muscle cells after the fitting of coronary stents.

Rapamycin is also an immunosuppressive agent which inhibits cycline, and may be used to prevent blood vessel restenosis.

According to the invention, the polymer layer may also be used to hold a heparin compound with a covalent bond, said compound giving it anticoagulant, antithrombotic and antorestenotic properties.

The invention also relates to a method to produce a bioactive implant as defined above. Said method comprises the following steps:

1) coat the substrate wherein the surface is made of a material chosen from metals, metallic alloys, semiconductor materials, conductive polymers, composite materials, ceramics, carbon fibres and their mixtures, with a polymer layer with reactive functions, and
2) fix a bioactive substance on the polymer layer by means of the reactive functions such that said substance can subsequently be released progressively on the implant site.

According to a first embodiment of the first step of the method according to the invention, the surface of the substrate is coated with a polymer, and the polymer is then modified to introduce the reactive functions.

According a second embodiment of said first step of the method according to the invention, the reactive function polymer is deposited directly onto the surface of the substrate.

The polymer layer may be deposited by any suitable means chosen according to the type of material composing the surface of the implant substrate.

In this way, if the surface of the substrate is made of an electricity conducting material, for example made of metal, metallic alloy, carbon fibres or conductive polymer, or semi-conductor material, the polymer may be deposited on said material by electropolymerisation using the surface of the substrate as the deposition electrode.

Electropolymerisation consists of the polymerisation of a monomer initiated electrochemically by electron transfer from the electrode surface to a monomer molecule or conversely. It results in the deposition of two types of polymers on the electrode surface, of very similar chemical structures, which are however easy to separate, as described in: P. Viel et al., Journal of Electroanalytical Chemistry, 470, 14 (1999) [5], in J. Charlier et el., Journal of Electroanalytical Chemistry 465, 200 (1999) [6], and in: C. Bureau et al., Journal of Adhesion, 58, 101, 1996 [7]. These two types of polymers are a polymer grafted chemically on the surface of the electrode, of a thickness between approximately 2 and 100 nm, and a non-grafted polymer, with a thickness of up to 40 μm. The non-grafted polymer may be eliminated by simply rinsing with a suitable solvent, while the grafted polymer withstands rinsing under ultrasound. The polymer formation mechanism currently accepted for cathodic electropolymerisation reactions consists of anionic propagation, either from the surface (grafted polymer) or directly in the solution (polymer in solution), both mechanisms being linked by a bifurcation, as described in the above-mentioned references and in: C. Bureau et al. Macromolecules, 30, 333 (1997) [8] (see also FIGS. 1 and 2). A similar cationic type mechanism is, however, recommended for the anodic polymerisation of vinyl monomers, as described in reference [6]. By means of the inclusion of cross-linking agents, the non-grafted polymer and the grafted polymer may be attached, and the deposition thickness controlled from 2 nm to 40 μm. This deposition method makes it possible to obtain a polymer coating on the conductive surface very strongly grafted by covalent bonding. Reactive functions may be implanted on said grafted polymer, either using monomers already with beneficial reactive functions (esters groups), or by carrying out the copolymerisation of said monomers with monomers functionalised by possibly protected functional groups, or by inducing the appearance of said functional groups with a subsequent chemical, electrochemical and/or radiochemical treatment.

If the polymer can be obtained from a monomer that can be polymerised using the anionic method, chosen for example from acrylonitrile, methacrylonitrile, 4-vinyl pyridine, 4-chlorostyrene, methyl methacrylate, ethyl methacrylate, their functionalised derivatives, epoxy group monomers, and copolymers obtained from said monomers, this consists of anionic polymerisation by cathodic electro-initiation.

If the polymer can be obtained from a monomer that can be polymerised using the cationic method, chosen for example from N-vinyl pyrrolidone, 4-vinyl pyridine, pyrrole, thiophene, aniline, or any monomer obtained by functionalising said base monomers, or any copolymer involving said monomers, this consists of cationic polymerisation by anodic electro-initiation.

According to the invention, the polymer deposited by electropolymerisation may form the reactive function polymer, or it may serve as an intermediate layer on which the reactive function polymer is subsequently deposited.

In the latter case, the reactive function polymer is then deposited on the polymer formed by electropolymerisation by radio-grafting or plasma polymerisation of a precursor monomer of said polymer.

Said second deposition may be performed, either by radio-grafting or by plasma polymerisation of a precursor polymer of the reactive function polymer.

Radio-grafting consists of forming, under the effect of ionising radiation, reactive sites on the polymer formed by electropolymerisation, from which the polymerisation of the monomers may be initiated. These sites are created by irradiation, for example using electrons, X rays, gamma rays or accelerated heavy ion beams. The irradiation may be performed before placing the polymer formed by electropolymerisation on the substrate in contact with the monomer or at the same time as the contact.

It is also possible to create monomer polymerisation sites on the polymer formed by electropolymerisation, by subjecting it to the effect of a plasma.

The polymerisation conditions are chosen so as to obtain a layer of polymer of suitable thickness on the intermediate layer formed by electropolymerisation on the implant substrate.

When reactive functions are introduced onto the polymer after the deposition of the layer on the substrate, this may be performed using conventional polymer functionalisation methods using suitable reactive functions. For example, in the case of polystyrene, the reactive functions may be introduced by fixation of chlorosulphonic acid which is then converted to introduce the required reactive functions.

If the surface of the substrate is made of other materials, for example of organic composite material, ceramic or carbon fibres, the polymer layer may be deposited on said substrate by grafting a precursor monomer by means of a plasma.

According to the invention, it is also possible, if necessary, to fix a heparin compound such as heparin onto the polymer layer. This may be performed during the radio-grafting of the precursor monomer of the polymer by adding heparin to the grafting medium containing the precursor monomer to be grafted. For this purpose, it is possible to use acrylic acid as the precursor monomer, to fix heparin, as described by Baquey et al, in "Innov. tech. Biol. Med., vol. 2, No. 4, 1981, page 378–389" [9].

In the last step of the method according to the invention, the reactive functions of the polymer layer are used to fix a bioactive substance such that it can subsequently be released on the implant site.

To carry out this fixation, it is possible to use microreservoirs or microcapsules fixed on the reactive functions of the polymer layer, said microreservoirs being filled with the bioactive substance and equipped with a wall enabling the release of said substance over a prolonged period. It is possible, for example, to fix the microreservoirs onto the polymer layer by means of functions associated with a microporous membrane surrounding the microreservoirs, said membrane being linked to the reactive functions of the polymer layer via a covalent bond.

Said microreservoirs may be agar microbeads filled directly with the bioactive substance, in the form a polymer pro-drug or spherulites, in turn filled with the bioactive substance. The agar microbeads are surrounded by a microfiltration membrane, for example made of polyacrylamide, which shows a microporosity such that it enables the passage of the active substance over a prolonged period.

Agar microbeads may be formed as follows.

Firstly, agar beads filled with the bioactive substance or spherulites are prepared by oil stream extrusion and the beads are introduced into a capillary tube where they are entrained by an oil stream and then coated with a photopolymerisable solution supplied by an adjacent capillary tube. The photopolymerisable solution may be for example based on acrylamide or bis-acrylamide and it is thus possible to form a polyacrylamide membrane around beads. The porosity of said membrane may be controlled by adjusting the bis-acrylamide concentration of the solution.

The microbeads are then fixed on the polymer layer which, in this case, may comprise COOH type reactive functions to form amide bonds between said COOH groups and amine groups added to the microbead polyacrylamide membrane. Said amine groups may be formed from hexamethylene diamine which is fixed onto the polyacrylamide using the hydrazine coupling technique.

Said coupling technique to a surface-grafted polymer using acrylic acid, of microbeads not filled with active substance is described by Degert et al., Biomat. Art. Cells & Immob. Biotech, 21(4), 1993, pages 553–561 [10].

Spherulites consist of lipid complex formed of inserted layers wherein or between which the bioactive substance is incorporated. In the body, the release of said substance is obtained by the action of endogenous lipases. The spherulites may also be fixed onto the polymer layer by means of polyacrylamide by suspending the spherulites in an agar solution that can be extruded and gelled in an oil stream in the form of beads subsequently circumscribed by a controllable permeability polyacrylamide membrane.

If the bioactive substance is a simple molecule such as aspirin, said molecule may be coupled chemically onto the reactive functions of the polymer layer by forming a compound capable of regenerating the bioactive substance on the implant site.

In the case of aspirin (acetylsalicylic acid), hydroxyl functions may be used as the reactive functions to form the corresponding ester, i.e. acetylsalicylate.

On the implant site, it will be possible to regenerate and release the bioactive substance by means of hydrolysis of the acetylsalicylate.

The hydroxyl function polymer may be for example poly(hydroxyethyl methacrylate), dextran or polyvinyl alcohol.

The bioactive substance may be fixed onto the polymer after the deposition of the polymer layer on the substrate or at the same time as said deposition.

In the latter case, the chemical coupling of the bioactive substance with a precursor monomer of the polymer intended to form the polymer layer is carried out beforehand and the polymer layer on which the bioactive substance is fixed is formed by polymerisation of the monomer coupled chemically with the bioactive substance or by copolymerisation of said monomer with a non-functionalised monomer.

In the case of acetylsalicylic acid fixed on poly (hydroxyethyl methacrylate), hydroxyl methacrylate acetyl salicylate is firstly prepared and then grafted onto the substrate, for example by radio-grafting.

The invention's other characteristics and advantages will be seen more clearly upon reading the following description, which is naturally given as an illustration and is not restrictive.

DETAILED DESCRIPTION OF THE EMBODIMENTS

EXAMPLE 1

This example illustrates the production of stents, comprising a metallic substrate coated with poly(methyl methacrylate) (PMMA) on which spherulites prepared by CAPSULIS, filled with antibiotic, are fixed.

An initial stainless steel (316 L) substrate is used and a polymethyl methacrylate coating is produced on said substrate by electropolymerisation. For this purpose, an electrolytic cell equipped with three electrodes, which are, respectively, a working electrode, a reference electrode and an auxiliary electrode, is used, the system being controlled by a potentiostat connected to a computer. The working electrode is composed of the metallic stent and an electrochemical solution is used comprising the monomer, methyl methacrylate (MM), dissolved at a rate of 30% by volume in a compatible solvent composed of dimethyl sulphoxide to which an electrolytic substrate salt composed of ammonium tetrabutyl perchlorate or ammonium tetrafluoroborate, at a concentration of $3.10^{-2}$ mol/l, has been added. The stent is placed as the working electrode in the electrolytic solution and deposition is carried out at a potential of −2.6 Volt (Ag+/Ag), i.e. with reference to a silver electrode as the reference electrode, with a polarisation time of 100 ms. The thickness of the film deposited is approximately 20 nm. After washing in ethanol and methyl isobutylketone, it is checked using electron microscopy emitted under the effect of X rays and using infrared spectrometry (reflection-absorption) that said film is indeed composed of methyl polymethacrylate.

Under these conditions, the polymerisation mechanism is an anionic mechanism which takes place in solution and on the surface.

The polymer formed in solution is eliminated by washing, while the surface polymer is grafted chemically onto the surface S of the electrode.

Spherulites filled with an antibiotic are then fixed onto said polymer layer using the procedure described below.

Firstly, 50 nm diameter spherulites filled with 12.5 mg of antibiotic per g of spherulites are prepared.

The spherulites filled with antibiotic are then suspended, at a concentration of 15% by volume, in a photoploymerisable solution comprising 15 to 20% by weight of acrylamide and 5% by weight of bis-acrylamide, the remainder being composed of the solvent, in this case, water containing $10^{-5}$ M of riboplasmin (photo-primer) and $10^{-3}$ M of N,N'-tetramethylene ethylene diamine TEMED (reduction agents).

Polyacrylamide beads are associated on the substrate coated with polymethyl methacrylate, after hydrolysing the polymethacrylate so that it comprises COOH reactive functions. In this way, covalent bonds are formed between the amine groups added to the polyacrylamide by coupling with the hexamethylene diamine and the polymethacrylic acid resulting from the hydrolysis of PMMA, which ensure the fixation of the spherulites and the antibiotic substance on the polymer layer.

EXAMPLE 2

In this example, a metallic stent is coated with poly(4-vinylpyridine) on which heparin is fixed. To carry out the deposition of the polymer, a solution containing 5 mol/l of 4-vinylpyridine and $5.10^{-2}$ mol/l of tetraethylammonium perchlorate in acetonitrile is used.

An electrochemical cell with three cells as described above is used, wherein the working electrode is composed of the stainless steel (316L) stent. The deposition is carried out by electropolymerisation at a potential of −2.8 Volt (Ag+/Ag), for a period of 40 s.

A poly(4-vinylpyridine) film of a thickness of 100 nanometres is obtained in this way. Said film is then modified by fixing heparin on it. For this purpose, the poly(4-vinylpyridine) is firstly quaternised by reacting with an acid or acid chloride, and then incubated in an aqueous sodium heparinate solution (specific activity equal to or approximately 160 IU/mg) containing a mass of heparin proportional to the area S of the substance to be coated at a rate of 10 $\mu$g of heparin/cm$^2$ (M is given in $\mu$g by the following formula where S is in cm$^2$: M=100 S $\mu$g).

After heparinisation of the substrate coated with poly(4-vinylpyridine), micro or nanoreservoirs filled with active ingredient may be fixed onto the poly(4-vinylpyridine) layer.

EXAMPLE 3

In this example, metallic stents coated with PMMA are used as in example 1, and polyacrylic acid is deposited onto said coating by grafting after plasma irradiation.

For this purpose, stents coated with PMMA are exposed to a plasma created by an RFGD (radiofrequency glow discharge) in a rarefied Argon/Oxygen atmosphere.

The procedure is carried out under the following conditions:

Ar/O2 mixture: 50/50

Pressure <10 mmHg

Radiofrequency: 13.45 MHz

Power <100 W.

After irradiation, the stents are placed in a reaction vessel containing a 20% (v/v) aqueous acrylic acid solution. The vessel is then placed in a thermostatically controlled chamber at a temperature of 65° for 5 hours.

The metallic stents coated with PMMA on which polyacrylic acid, the quantity of which is evaluated by titration of the —COOH functions (some $10^{-5}$ moles per mm$^2$), is grafted, are then taken out.

Spherulites filled with active ingredient are then fixed on the polyacrylic acid layer according to the procedure in example 1.

EXAMPLE 4

This example illustrates the production of a metallic stent coated with PMMA as in example 1 and a layer of poly (hydroxyethyl methacrylate) on which aspirin (acetyl salicylic acid) is fixed.

Hydroxyethyl methacrylate acetylsalicylate is firstly prepared by esterification of the hydroxyethyl methacrylate with acetylsalicylic acid.

Said acetylsalicylate is then grafted onto the stent coated with PTFE as in example 3 by replacing part of the acrylic acid by hydroxyethyl methacrylate acetylsalicylate.

In this way, a stent, on which aspirin is fixed, is obtained and may subsequently be released by hydrolysis on the stent implant site.

REFERENCES

[1]: EP-A-596 615
[2]: EP-A-0 873 732
[3]: U.S. Pat. No. 4 879 135
[4]: EP-A-0 832 618
[5]: P. Viel et al., Journal of Electroanalytical Chemistry, 470, 14 (1999)
[6]: J. Charlier et el., Journal of Electroanalytical Chemistry 465, 200 (1999)
[7]: C. Bureau et al., Journal of Adhesion, 58, 101, 1996.
[8]: C. Bureau et al. Macromolecules, 30, 333 (1997).
[9]: Baquey et al, Innov. tech. Biol. Med., vol. 2, No. 4, 1981, pages 378–389
[10]: Degert et al., Biomat. Art. Cells & Immob. Biotech, 21(4), 1993, pages 553–561.

What is claimed is:

1. Bioactive implant comprising a substrate wherein a surface is made of an electrically conductive material chosen from metals, metallic alloys, semi-conductor materials, conductive polymers, composite materials, ceramics, carbon fibres or their mixtures, said surface being coated with a polymer or copolymer layer with reactive functions grafted by means of a covalent bond on the substrate surface, said layer having reactive functions and being grafted by electrocopolymerization, and a bioactive substance fixed on the implant by means of said reactive functions to enable progressive release on an implant site.

2. Implant according to claim 1, wherein the substrate surface is made of stainless steel, cobalt or titanium-based alloy, noble metal, noble metal alloy or shape-retentive alloy.

3. Implant according to claim 1, wherein the reactive functions of the polymer of the layer are chosen from the acid, ester, amide, amine or hydroxyl functions.

4. Implant according to claim 1, wherein the reactive function polymer or copolymer is chosen from vinyl monomer polymers and/or copolymers, functionalised or not, dextran, conductive polymers or any polymer or copolymer formed from mixtures of vinyl monomers and/or conductive polymer precursor monomers, functionalised or not.

5. Bioactive implant according to claim 1, wherein the bioactive substance is fixed on the polymer or copolymer layer by means of microreservoirs containing said substance fixed on the reactive functions of the polymer or copolymer layer.

6. Bioactive implant according to claim 5, wherein the microreservoirs comprise a microporous outer membrane which is coupled with the reactive functions of the polymer or copolymer layer.

7. Implant according to claim 6, wherein the membrane is made of polyacrylamide.

8. Implant according to claim 5, wherein the microreservoirs are agar beads filled directly with the bioactive substance or filled with spherulites in turn filled with the bioactive substance.

9. Implant according to claim 1, wherein the bioactive substance is chosen from antimitotic, antiaggregation, antiinflammatory, antirestenotic, antithrombotic, immunosuppressive, antirejection compounds, antibiotic compounds or reverse oligonucleotides.

10. Implant according to claim 9, wherein the bioactive substance is chosen from cyclosporin, rapamycin, aspirin, ticlopidine, 3-deazaadenosine or MCP-1.

11. Implant according to claim 1, wherein the polymer or copolymer layer is also used to hold a heparin compound with a covalent bond.

12. Method to produce a bioactive implant according to claim 1, comprising the following steps:
   i. coating the substrate wherein the surface is made of an electrically conductive material chosen from metals, metallic alloys, semi-conductor materials, conductive polymers, composite materials, ceramics, carbon fibres or their mixtures, said coating being by grafting with a layer of a polymer or copolymer with reactive functions by means of a covalent bond, said layer having reactive functions being grafted by electropolymerization, and
   ii. fix a bioactive substance on the polymer or copolymer by means of the reactive functions such that said substance can subsequently be released progressively on the implant site.

13. Method according to claim 12, wherein, in step 1, the surface of the substrate is coated with a polymer or copolymer and the polymer or copolymer is then modified to introduce the reactive functions.

14. Method according to claim 12, wherein, in step 1, the reactive function polymer or copolymer is deposited directly onto -he surface of the substrate.

15. Method according to claim 12, wherein the polymer deposited by electropolymerization is the reactive function polymer.

16. Method according to claim 12, wherein, a heparin compound is also fixed onto the reactive function polymer or copolymer layer.

17. Method according to claim 12, wherein the fixation of the bioactive substance on the reactive functions of the polymer or copolymer layer consists of coupling said substance chemically onto the reactive functions by forming a compound capable of regenerating the bioactive substance on the implant site.

18. Method according to claim 17, wherein the reactive functions are hydroxyl functions and the bioactive substance is acetylsalicylic acid.

19. Method according to claim 18, wherein the reactive function polymer layer is chosen from poly(hydroxyethyl methacrylate), dextran or polyvinyl alcohol.

20. Method according to claim 17, wherein, the chemical coupling of the bioactive substance with a precursor monomer of the polymer or copolymer intended to form the polymer layer is carried out beforehand and the polymer layer on which the bioactive substance is fixed is formed by polymerisation of the monomer coupled chemically with the bioactive substance or by copolymerisation of said monomer with a non-functionalised monomer.

21. Method according to claim 12, wherein, the bioactive substance is fixed on the polymer or copolymer layer by means of microreservoirs containing said substance fixed on the reactive functions of the polymer or copolymer layer.

22. Method according to claim 21, wherein, the microreservoirs are fixed onto the polymer or copolymer layer by means of functions associated with a microporous membrane surrounding the microreservoirs, said membrane being linked to the reactive functions of the polymer or copolymer layer via a covalent bond.

23. Method according to claim 22, wherein the membrane is made of polyacrylamide.

24. Method according to claim 21, wherein the microreservoirs are agar beads filled directly with the bioactive substance or filled with spherulites in turn filled with the bioactive substance.

* * * * *